United States Patent
Bouwstra et al.

(10) Patent No.: US 9,192,298 B2
(45) Date of Patent: Nov. 24, 2015

(54) CONTACT LENS FOR INTRAOCULAR PRESSURE MEASUREMENT

(71) Applicant: Syntec Technologies, Inc., Pavilion, NY (US)

(72) Inventors: Siebe Bouwstra, Amsterdam (NL); Alok Kapoor, Weston, MA (US)

(73) Assignee: Syntec Optics, Pavilion, NY (US)

( * ) Notice: Subject to any disclaimer, the term of this patent is extended or adjusted under 35 U.S.C. 154(b) by 210 days.

(21) Appl. No.: 14/019,587

(22) Filed: Sep. 6, 2013

(65) Prior Publication Data

US 2015/0073253 A1 Mar. 12, 2015

(51) Int. Cl.
- *A61B 3/16* (2006.01)
- *G02C 7/04* (2006.01)
- *G02C 7/08* (2006.01)

(52) U.S. Cl.
CPC ... *A61B 3/16* (2013.01); *G02C 7/04* (2013.01); *G02C 7/083* (2013.01)

(58) Field of Classification Search
CPC ........... A61B 3/16; G02C 7/049; G02C 11/10
USPC ....................................................... 600/398
See application file for complete search history.

(56) References Cited

U.S. PATENT DOCUMENTS

| | | | |
|---|---|---|---|
| 4,922,913 A | 5/1990 | Waters, Jr. et al. | |
| 5,160,463 A | 11/1992 | Evans et al. | |
| 6,579,235 B1 | 6/2003 | Abita et al. | |
| 6,834,955 B2 | 12/2004 | Doshi | |
| 7,137,952 B2 | 11/2006 | Leonardi et al. | |
| 2002/0196409 A1 | 12/2002 | Jani | |
| 2008/0062381 A1 | 3/2008 | Doshi et al. | |
| 2009/0243125 A1 | 10/2009 | Pugh et al. | |
| 2010/0234717 A1 | 9/2010 | Wismer | |
| 2011/0184271 A1 | 7/2011 | Veciana et al. | |
| 2011/0288395 A1 | 11/2011 | Elsheikh et al. | |
| 2012/0277568 A1 | 11/2012 | Chiou et al. | |

(Continued)

FOREIGN PATENT DOCUMENTS

| EP | 1 262 307 A2 | 12/2002 |
|---|---|---|
| EP | 2 122 638 B1 | 11/2009 |

(Continued)

OTHER PUBLICATIONS

Entenmann et al., "Contact Lens Tonometry—Application in Humans", Investigative Ophthalmology & Visual Science, 38 (1997) 2447-2451.

(Continued)

*Primary Examiner* — Brian Szmal
(74) *Attorney, Agent, or Firm* — Louis S. Horvath

(57) ABSTRACT

A monitoring apparatus for the eye has a soft contact lens formed of a transparent substrate having an inner surface that faces the eye and an outer surface. A first arcuate pattern of resistive traces is formed onto the outer surface of the lens substrate and centered about the center of the lens. A second arcuate pattern of resistive traces is formed onto the inner surface of the lens substrate and centered about the center of the lens. One or more conductive traces connects the first pattern to the second pattern. A signal monitor is in signal communication with the first and second arcuate patterns of resistive traces and provides a signal indicative of the lens shape according to electrical current through the first and second arcuate patterns of resistive traces.

17 Claims, 23 Drawing Sheets

(56) References Cited

U.S. PATENT DOCUMENTS

2012/0289810 A1* 11/2012 Ehrecke .................. 600/398
2013/0041245 A1* 2/2013 Cerboni .................. 600/398

FOREIGN PATENT DOCUMENTS

| EP | 2 412 305 | 2/2012 |
|---|---|---|
| WO | WO 03/018307 A1 | 3/2003 |
| WO | WO 03/088867 A2 | 10/2003 |
| WO | WO 2009/049686 A1 | 4/2009 |
| WO | WO 2009/123985 A1 | 10/2009 |
| WO | WO2011083105 A1 | 7/2011 |

OTHER PUBLICATIONS

Laukhin et al. "Non-invasive IOP monitoring with a contact lens engineered with a nanostructured polymeric sensing film", Sensors and Actuators A 170 (2011) 36-43.

J. Hjortdal and P. K. Jensen, "In vitro measurement of corneal strain, thickness, and curvature using digital image processing," Acta Ophthalmol. Scand., vol. 73, pp. 5-11, 1995.

A. K. C. Lam and W. A. Douthwaite, "The effect of an artificially elevated intraocular pressure on the central corneal curvature," Ophthalmic Physiol. Opt., vol. 17, pp. 18-24, 1997.

Chen, Rodger, Agrawal, Saati, Meng, Varma, Humayun, Tai, "Implantable micromechanical parylene-based pressure sensors for unpowered IOP sensing" Journal of Micromechanics and Microengineering, (2007) 17, pp. 1931-1938.

Fonseca, Allen, Kroh, White, "Flexible Wireless Passive Pressure Sensors for Biomedical Applications", Solid-State Sensors and Systems Workshop, Hilton Head Island, SC, Jun. 2006.

Yan, "An unpowered, wireless contact lens pressure sensor for point-of-care glaucoma diagnosis", IEEE EMBS Conference, 2011, 2522-2525.

R. Puers, G. Vandevoorde, and D. De Bruyker, "Electrodeposited copper inductors for intraocular pressure telemetry," J. Micromech. Microeng., vol. 10, pp. 124-129, 2000.

U. Schnakenberg, P. Walter, G. Vom Bögel, C. Krüger, H. C. Lüdtke-Handjery, H. A. Richter, W. Specht, P. Ruokonen, and W. Mokwa, "Initial investigations on systems for measuring intraocular pressure," Sens. Actuators, vol. 85, pp. 287-291, 2000.

K. Stangel, S. Kolnsberg, Hammerschmidt, H. K. Trieu, and W. Mokwa, "A programmable Intraocular CMOS pressure sensor system Implant," IEEE J. Solid State, vol. 36, No. 7, pp. 1094-1100, Jul. 2001.

Parviz, Babak, "For Your Eye Only", IEEE Spectrum, Sep. 2009. pp. 36-41.

Sensimed Triggerfish brochure "Continuous Monitoring of IOP up to 24 Hours", (3 pages) Sensimed, Inc., 2012.

Sensimed, white paper, Principles and rationale for the Sensimed Triggerfish (R) Sensor device. (2 pages) Sensimed, Mar. 2011.

Groves, Nancy "Sensor yields 24-hour IOP record" Ophthalmology Times, Aug. 2012. pp. 20-21.

K. Mansouri, T. Shaarawy, "Continuous intraocular pressure monitoring with a wireless ocular telemetry sensor: initial clinical experience in patients with open angle glaucoma", British Journal of Ophthalmology, 2011: 96 pp. 627-629.

Leonardi M, Leuenberger P, Bertrand D, et al. First steps toward noninvasive intraocular pressure monitoring with a sensing contact lens. Invest Ophthalmol Vis Sci 2004:45:3113-17.

M. Leonardi, P. Leuenberger, D. Batrand, A. Bertsch, and P. Renaud, "A soft contact lens with a mems strain gage embedded for intraocular pressure monitoring," in Proc. 12th Int. Conf. Solid State Sensors, Actuators, Microsyst., Boston, MA, Jun. 8-12, 2003, vol. 2, pp. 1043-1046.

Leonardi M, Pitchon EM, Bertsch A, et al. Wireless contact lens sensor for intraocular pressure monitoring: assessment on enucleated pig eyes. Acta Ophthalmol 2009;87:433-7.

* cited by examiner

CONTACT LENS FOR INTRAOCULAR PRESSURE MEASUREMENT

FIELD OF THE INVENTION

This invention generally relates to ophthalmic measurement devices and more particularly relates to a monitoring device for non-invasive monitoring of intraocular pressure.

BACKGROUND OF THE INVENTION

Intraocular pressure (IOP) is measured as an indicator of glaucoma and other conditions of the eye. IOP indicates the pressure that is exerted by the ocular fluid called "aqueous humor" that fills the anterior chamber of the eye. Normal IOP is in the range of 10-21 mmHg. Elevated IOP is associated with loss of optic nerve tissue, loss of peripheral vision, and leads to blindness if not treated. IOP measurement, optic disc examination, and visual field testing are used for glaucoma diagnosis. Regular monitoring of the above three parameters is highly useful for disease detection and management. Early treatment helps to slow disease progression. However, early signs are detectable only by a physician.

Conventional quantification of IOP measures the resistance of the cornea to indentation or applanation, using a device such as the Goldmann Applanation Tonometer (GAT). The GAT measurements are accurate to within 0.5 mmHg for IOPs of 20 mmHg or lower. While this provides some measure of accuracy in measuring IOP for most individuals, however, the GAT device has a number of shortcomings that limit its effectiveness for diagnosis and monitoring purposes. The GAT can only be used in the doctor's office, making it unsuitable for overnight use or longer term monitoring. Central corneal thickness affects the measurement of IOP by the GAT device. A thinner cornea than normal would applanate to a higher degree than normal, thereby providing underestimation of the pressure. Similarly, a thicker cornea than normal would provide an overestimate of the IOP.

Significantly, the GAT device and other instruments that measure IOP are not suitable for continuous IOP measurement. IOP fluctuations are known to occur but are not readily detectable using standard office measurement practice. Thus, there is a need for a measurement apparatus that allows monitoring of patient IOP over a period ranging from a few hours to a day or longer.

There have been a number of attempts to address the need for more portable IOP measurement devices, including those using various types of contact lens or other wearable device for noninvasive measurement. One type of device forms a wire strain gauge on an intermediate medium, affixes the intermediate medium within a semirigid holder or contact lens, and obtains periodic measurements therefrom. The strain gauge may use a Wheatstone bridge, LC circuit, or other arrangement of devices to provide a signal that indicates changes in the intraocular pressure measurement of the wearer.

Although various types of wearable device have been proposed, however, significant difficulties remain. Even where the proposed solutions are workable, for example, high complexity in manufacturing leads to high cost. Significantly, the proposed solutions do not readily lend themselves to customization, so that lenses made using these methods are difficult to fabricate for individual patients. Fabrication of a custom contact lens or other wearable device for IOP measurement can thus take considerable time, causing delay in obtaining measurement data and further driving up the cost of the measurement device. Furthermore, the accuracy of existing strain-gauge solutions and their suitability for full-fledged diagnostic use has also been questioned.

Thus, it can be seen that there is a need for apparatus and methods for fabricating a wearable lens that can be inexpensively manufactured and customized to provide accurate, noninvasive 24 hour monitoring of IOP for a patient.

SUMMARY OF THE INVENTION

It is an object of the present invention to address need for a wearable measurement apparatus that can be inexpensively manufactured and customized to provide accurate, noninvasive 24 hour monitoring of IOP for a patient.

It is a feature of the present invention that it offers enhanced sensitivity over other proposed solutions. Embodiments of the present invention provide wearable measurement devices that can be more readily fabricated and customized for different users.

It is an advantage of the present invention that it provides a wearable measurement device having enhanced accuracy over conventional solutions.

According to an embodiment of the present invention there is provided a monitoring apparatus for the eye, comprising:
  a) a soft contact lens formed of a transparent substrate having an inner surface that faces the eye of a patient and an outer surface opposite the inner surface and having a center;
  b) a first arcuate pattern of resistive traces formed onto the outer surface of the lens substrate and wherein the first arcuate pattern is centered about the center of the lens;
  c) a second arcuate pattern of resistive traces formed onto the inner surface of the lens substrate and wherein the second arcuate pattern is centered about the center of the lens;
  d) one or more conductive traces formed on the lens that connect traces of the first pattern to traces of the second pattern, and
  e) a signal monitor that is in signal communication with the first and second arcuate patterns of resistive traces and that provides a signal indicative of the lens shape according to electrical current through the first and second arcuate patterns of resistive traces.

These and other aspects, objects, features and advantages of the present invention will be more clearly understood and appreciated from a review of the following detailed description of the preferred embodiments and appended claims, and by reference to the accompanying drawings.

BRIEF DESCRIPTION OF THE DRAWINGS

While the specification concludes with claims particularly pointing out and distinctly claiming the subject matter of the present invention, it is believed that the invention will be better understood from the following description when taken in conjunction with the accompanying drawings, wherein:

DETAILED DESCRIPTION OF THE INVENTION

The present description is directed in particular to elements forming part of, or cooperating more directly with, apparatus in accordance with the invention. It is to be understood that elements not specifically shown or described may take various forms well known to those skilled in the art.

Where they are used, the terms "first", "second", and so on, do not necessarily denote any ordinal, sequential, or priority relation, but are simply used to more clearly distinguish one element or set of elements from another, unless specified otherwise.

As used herein, the term "energizable" relates to a device or set of components that perform an indicated function upon receiving power and, optionally, upon receiving an enabling signal.

In the context of the present disclosure, two elements are considered to be substantially orthogonal if their angular orientations differ from each other by 90 degrees +/−12 degrees.

The term "actuable" has its conventional meaning, relating to a device or component that is capable of effecting an action in response to a stimulus, such as in response to an electrical signal, for example.

In the context of the present disclosure, the term "oblique" means at an angle that is not an integer multiple of 90 degrees. Two beams, for example, are considered to be oblique with respect to each other if they diverge from or converge toward each other at an angle that is at least about 2 degrees or more away from parallel, or at least about 2 degrees or more away from orthogonal.

Embodiments of the present invention provide a solution for non-invasive IOP measurement using contact lens deformation. By comparison with earlier attempts to address this problem, embodiments of the present invention provide a contact lens having improved mechanical properties that allow enhanced measurement sensitivity. Embodiments of the present invention use inkjet or other 3-dimensional (3-D) printing methods to form a pattern of traces onto one or both sides of a contact lens for providing a strain gauge that has enhanced sensitivity over sensing devices formed using alternative methods. Improvements in overall lens geometry are also provided to help provide an added range of movement of the lens curvature to correspond to changes in intraocular pressure.

Contact Lens Design

Figure 1A:
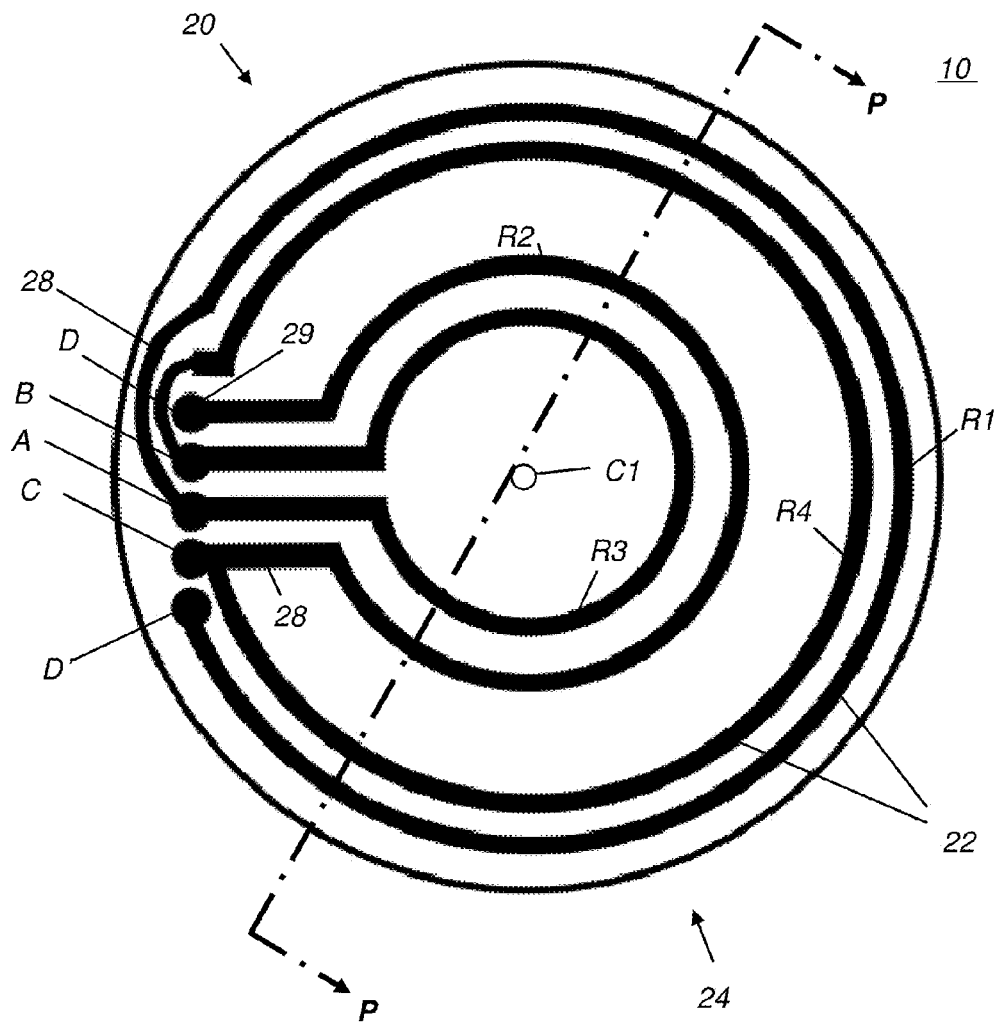
FIG. 1A is a top view that shows a contact lens having, on the top surface, a pattern of traces that provide a strain gauge such as a Wheatstone bridge.
Figure 1B:
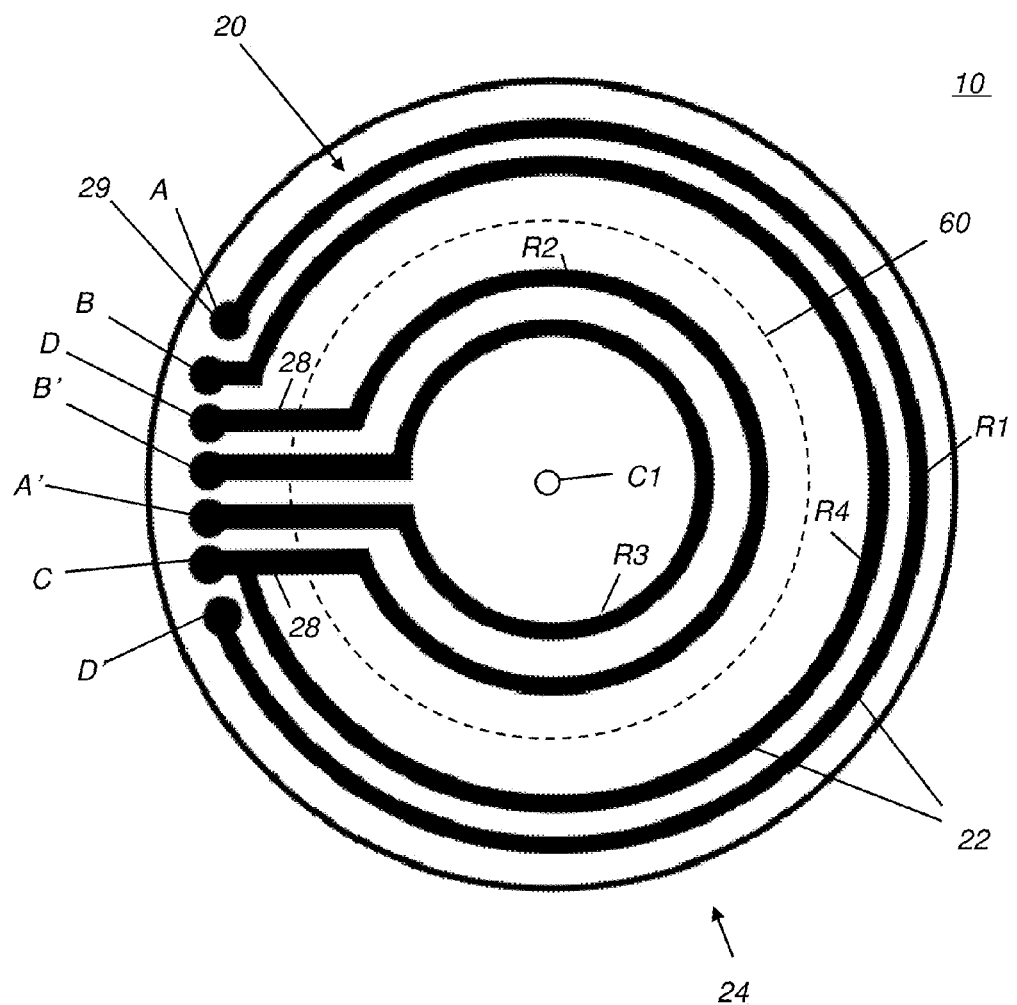
FIG. 1B is a top view that shows a contact lens with a strain gauge according to an alternate embodiment of the present invention.

FIGS. 1A and 1B are top views that show a contact lens 10 having an arcuate pattern of resistive traces 22 that form resistors R1, R2, R3, and R4, wherein the arcuate traces are substantially concentric about a center C1. Resistors R1, R2, R3, and R4 provide a strain gauge 20 on the top side of lens 10. Conductive traces 28 connect resistive traces 22 to terminals A, B, C, and D, which relate to strain gauge 20 components and connections as described in more detail subsequently. According to an embodiment of the present invention, center C1 is a center of symmetry for the lens 10. However, center C1 can be offset from the geometric center of symmetry.

For strain gauge 20 embodiments described herein, terminals 29 may be described by capital letters A, B, C, and D or capital letters having an appended apostrophe, such as B', D' and so on. The capital letter indicates the terminal's function in an electrical circuit, as described in more detail subsequently. Terminals labeled B are electrically equivalent to terminals labeled B', but at a different location; terminals labeled D are electrically equivalent to terminals labeled D', but are each at a different location.

By way of example and not by limitation, and for reference, the relative position of a limbus 60 for the patient's eye is shown in FIG. 1B. Resistors R1 and R4 are considered to lie outside limbus 60; resistors R2 and R3 lie within limbus 60.

FIG. 1B shows contact lens 10 having contact patterns and conductive traces 28 and resistive patterns 22 according to an alternate embodiment of the present invention. Terminals A, B, C, D, A', B' and D' show where bond pads or metallizations for wire bonding, flip-chip bonding, or other connections are made.

By way of example and not by limitation, and for reference, the relative position of a limbus 60 for the patient's eye is shown in this figure. Resistors R1 and R4 are considered to lie outside limbus 60; resistors R2 and R3 lie within limbus 60.

Figure 1C:
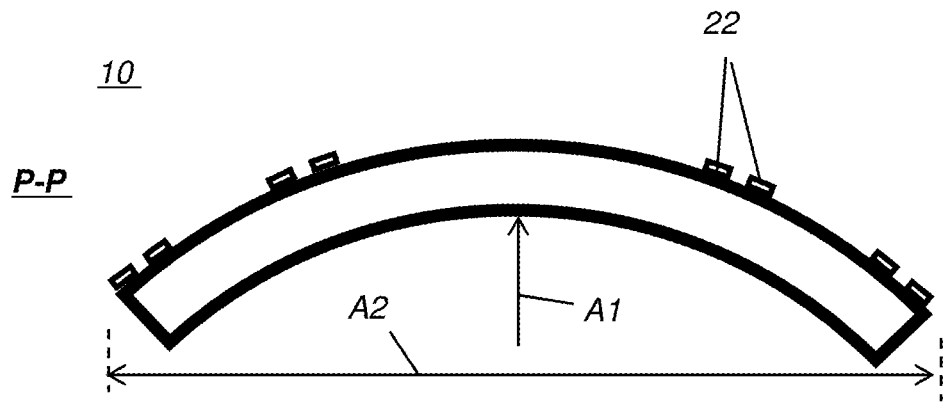
FIGS. 1C and 1D show the same contact lens at two different curvatures, indicating two different IOP conditions.
Figure 1D:
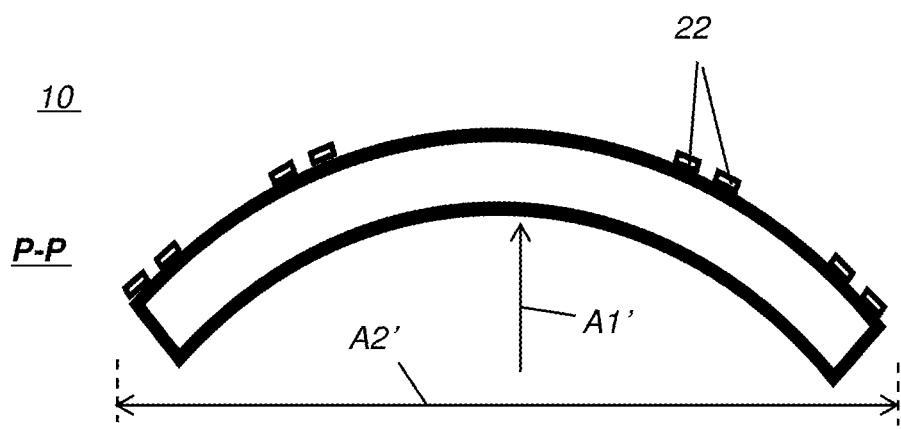

The cross-sectional side views of FIGS. 1C and 1D, referenced to line P-P of FIG. 1A, show the same contact lens 10 at two different curvatures, indicating two different IOP conditions. In FIG. 1D, for example, the lens curvature is more pronounced over that of FIG. 1C, so that the center of lens 10 is raised, as indicated by arrows A1' and A1, respectively. The width of contact lens 10 in FIGS. 1C and 1D, indicated by arrows A2 and A2', changes correspondingly. Strain gauge 20 yields a different output signal for each of the two positions shown in FIGS. 1C and 1D, due to deformation of the lens, indicative of the IOP.

Figure 2:
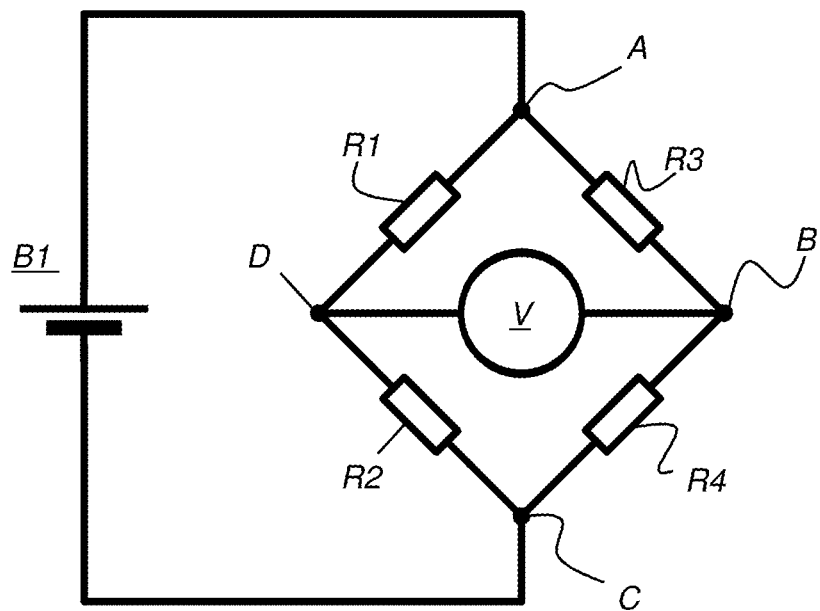
FIG. 2 shows a schematic diagram of a Wheatstone bridge.

According to an embodiment of the present invention, strain gauge 20 is a full Wheatstone bridge. FIG. 2 shows a schematic diagram of a Wheatstone bridge. This arrangement provides voltage from a battery B1 across terminals A and C to a set of closely matched resistors R1, R2, R3, and R4. Resistors R1 and R2 are paired as a first voltage divider; resistors R3 and R4 are similarly paired as a second voltage divider. Any slight mismatch between the voltage across terminals B and D is an output voltage V that indicates some type of change or other type of movement, such as change in IOP value according to an embodiment of the present invention.

Figure 3A:
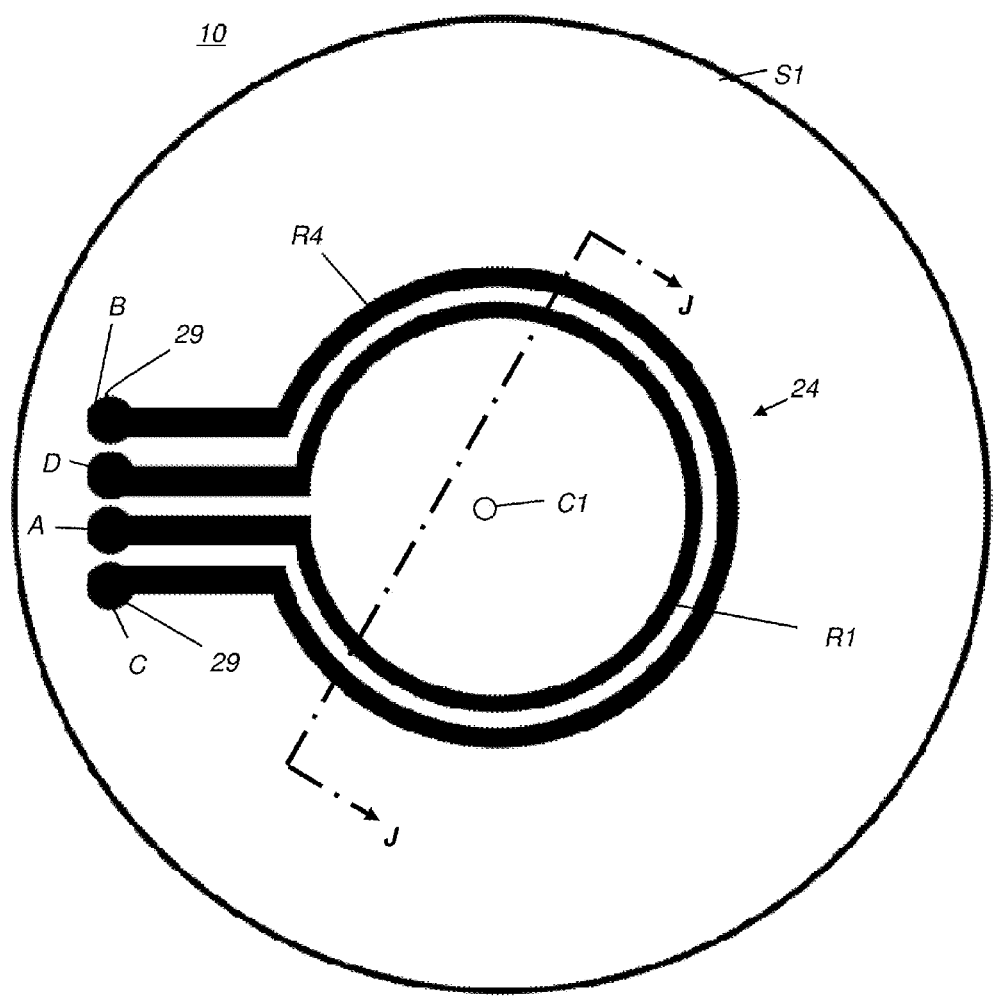
FIG. 3A shows the use of the outer surface for forming a first portion of the conductive pattern of traces according to an embodiment of the present invention.
Figure 3B:
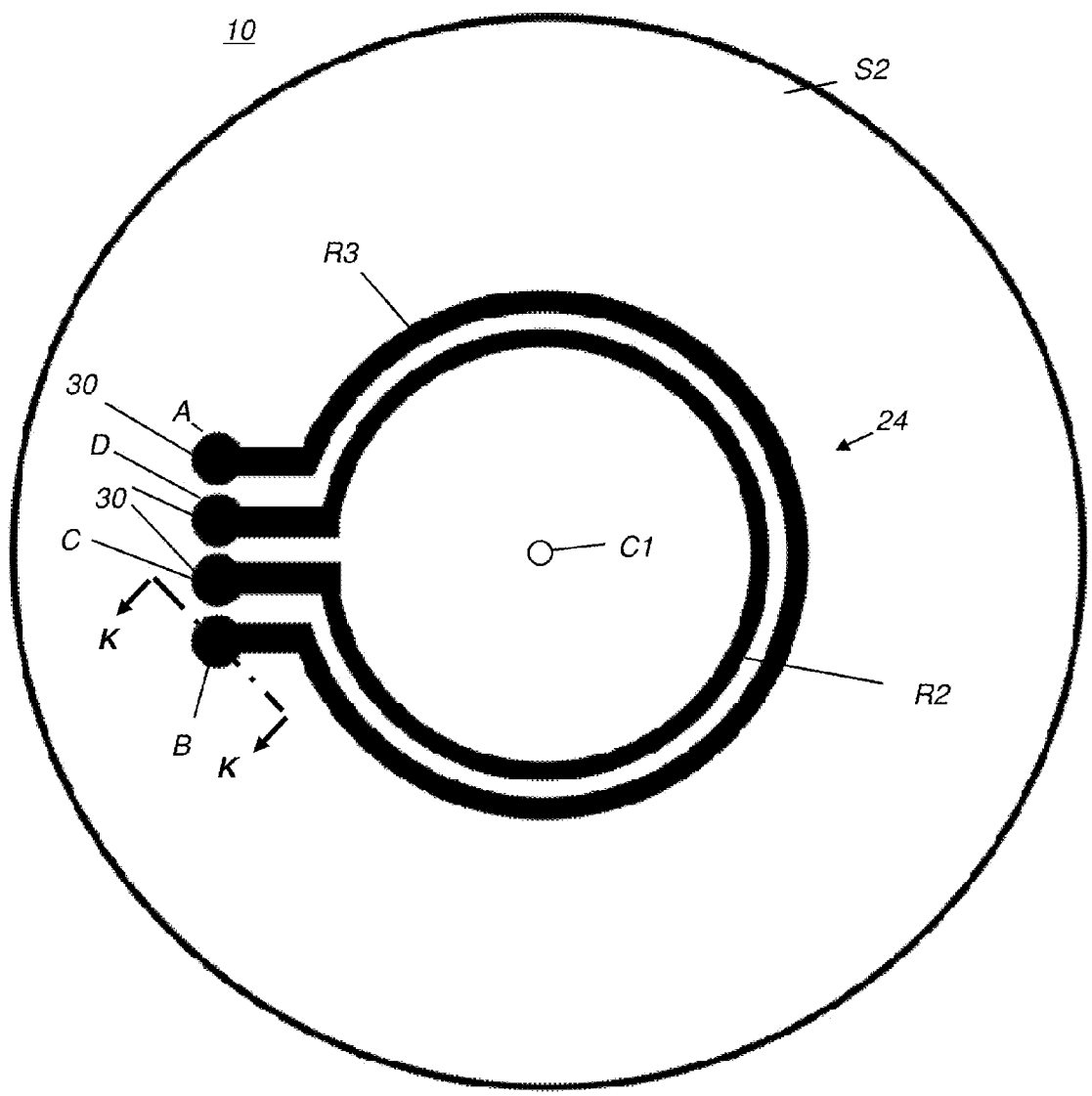
FIG. 3B shows the use of the inner surface for forming a second portion of the resistive and conductive pattern of traces that work with the pattern of traces shown in FIG. 3A.

As shown in FIGS. 1A and 1B, resistors R1, R2, R3, and R4 are provided by resistive traces 22 that are formed in an arcuate pattern onto either one or both outer and inner surfaces of lens 10. In the embodiment shown in FIGS. 1A and 1B, these arcuate resistive traces 22 are only on the outer surface (top) of lens 10. FIGS. 3A and 3B show, by way of alternate example, the use of both outer surface S1 and inner surface S2 of lens 10. In FIG. 3A, a pattern 24 of resistors R1 and R4 is formed on the outer surface S1 of lens 10. FIG. 3B shows resistors R2 and R3 formed in an arcuate pattern 26 on the back or inner surface S2 of lens 10, about center C1. Vias 30 connect inner surface S2 with outer surface S1, as described in more detail subsequently.

Figure 3C:
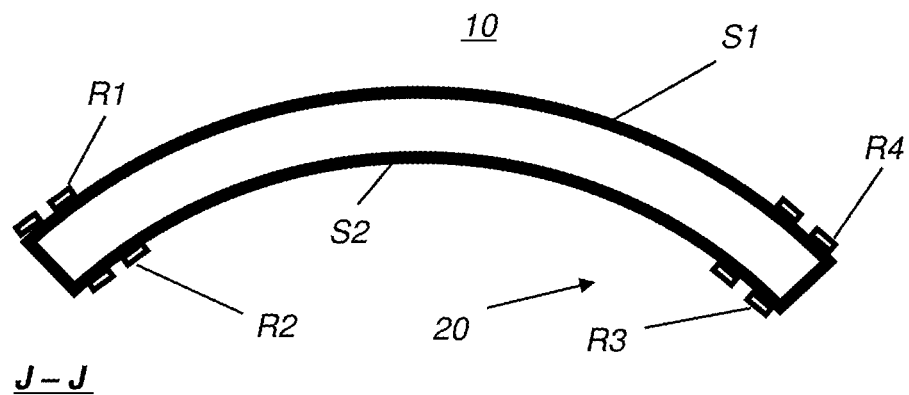
FIGS. 3C and 3D show a cross-sectional side view of an embodiment that has resistive traces on both surfaces of a lens, with different curvatures.
Figure 3D:
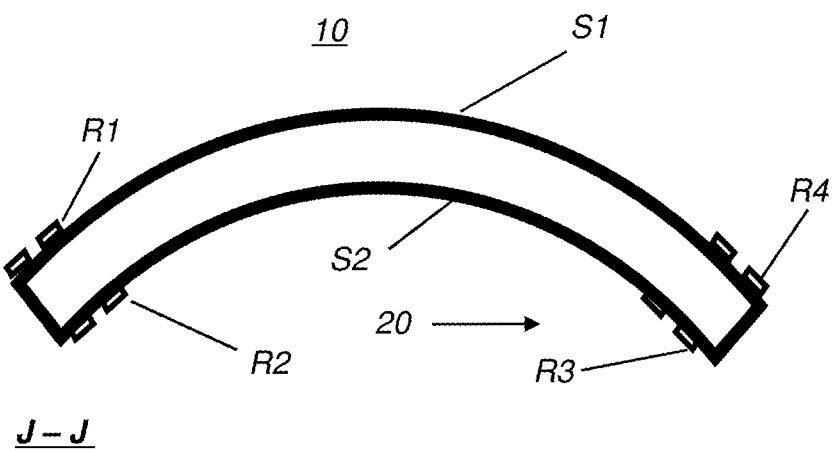

FIGS. 3C and 3D show a cross-sectional side view of an embodiment of lens 10 of the present invention, referenced to line J-J in FIG. 3A. Lens 10 has resistive traces on both surfaces S1 and S2 of the lens 10 substrate, with different curvatures for lens 10 itself, indicating different IOP values. In this arrangement providing a Wheatstone bridge, the lens 10 substrate is used to separate the two elements of each respective resistor pair, separating resistor R1 from R2 and resistor R3 from R4.

With respect to the eye of the patient, one or more of resistors R1-R4 can be positioned to lie either inside or outside the limbus, as described previously with reference to FIG. 1A. For the single-sided trace embodiment of FIG. 1A, for example, signal sensitivity of the Wheatstone bridge may be enhanced with R1 and R4 close together, such as outside the limbus 60, and resistors R2 and R3 close together, such as inside the limbus 60. With respect to the Wheatstone bridge circuit arrangement of FIG. 2, the highest sensitivity to bending is measured when resistors R1 and R4 change value in one direction, so that both simultaneously increase in resistance and voltage or both decrease in resistance and voltage, and where resistors R2 and R3 correspondingly change value in the opposite direction.

Forming traces on both surfaces S1 and S2 of the lens 10 substrate is advantageous for a number of reasons. This arrangement helps to enhance the overall sensitivity of the gauges 20, since the inner surface S1 and outer surface S2 of the lens 10 substrate change shape partly in opposing directions with a change in intraocular pressure, associated with bending of the lens. According to an embodiment of the present invention, traces on opposite surfaces are visually aligned or superimposed, so that, with respect to a top view of the lens (such as the views shown in FIGS. 1A, 1B, 3A, and 3B), traces on surface S2 are substantially aligned with traces on surface S1 and, therefore, can't be discerned from traces on top surface S1 by the patient who wears the lens. This arrangement reduces possible obstruction of view, since visually superimposed traces effectively occupy less of the visual field. This arrangement also has other advantages, tending to provide a more accurate measure of bending strain over a particular portion of the lens 10, canceling possible common-mode factors, such as might be due to temperature effects, for example. For a gauge 20 having four resistive traces 22, for example, a visually aligned or superimposed trace arrangement allows only two traces to be visible from either side. This arrangement also allows more flexibility for trace shape and placement. Separation between traces can be extended over trace patterns shown in other proposed solutions, since half of the traces can be formed on each of sides S1 and S2. In the two-sided embodiment, there are multiple possible arrangements for resistors. For example, all resistors can be placed inside the limbus, or all resistors can lie outside the limbus. Other arrangements with two resistors inside and two resistors outside the limbus can alternately be used.

Figure 4A:
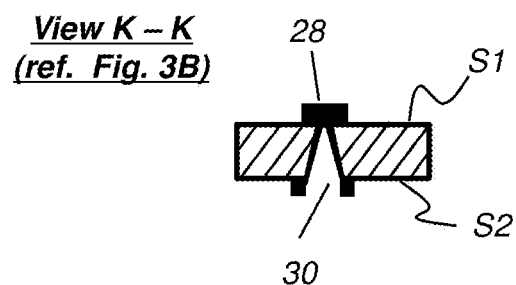
FIG. 4A shows, for an enlarged area, a via connection between outer and inner patterns schematically.

In order to use resistive traces on both inner and outer surfaces, connections must be made between the pattern of traces on each surface. FIG. 4A shows a conceptual cross sectional, enlarged view in which a via 30 in a through-hole between the outer surface S1 and inner surface S2 trace patterns is provided. Vias 30 are formed by adding a conductive material to the sidewalls and rims of a hole that is formed in the lens. FIG. 4A shows via 30 connection to outer and inner surface S1 and S2 patterns in a cross section view, referenced to line K-K in FIG. 3B.

Figure 4B:
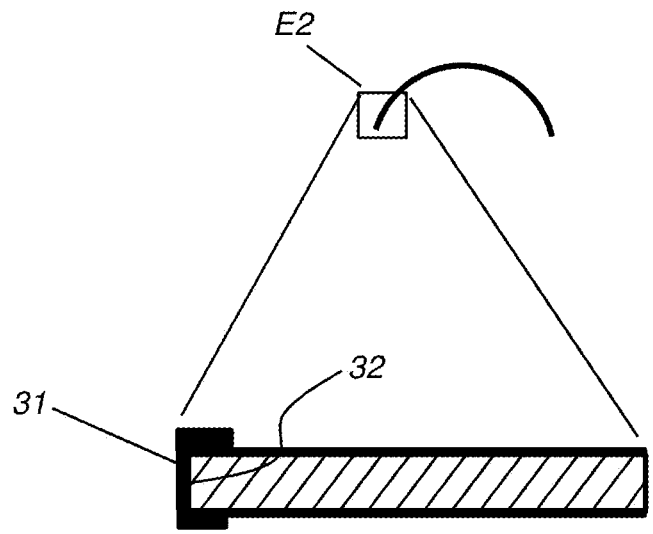
FIG. 4B shows connection between patterns of traces using a wrap-around conductive trace.

FIG. 4B shows providing a connection between patterns on opposite surfaces using an alternative approach. Here, as shown in an enlarged area view E2, connection is made using a wrap-around conductive trace via 31 that wraps about the edge 32 along the outer periphery of lens 10. Optionally, edge 32 can be featured with indents, so that vias 31 at the rim fit within the perimeter of the lens 10.

Figure 5A:
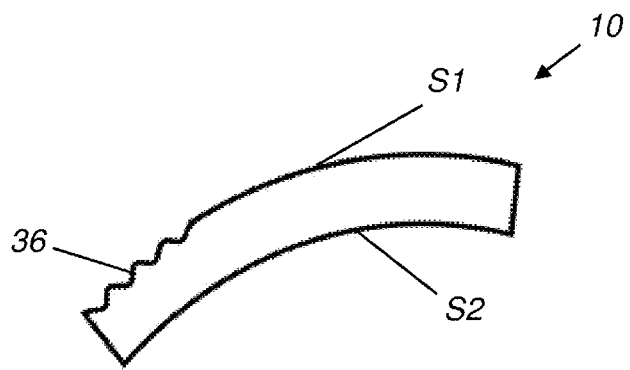
FIG. 5A shows a cross-sectional view of a lens with grooves.
Figure 5B:
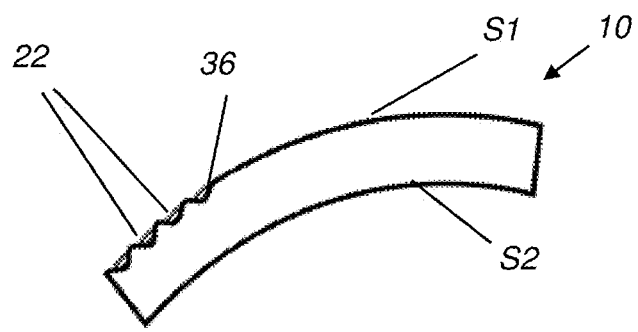
FIG. 5B shows a cross-sectional view of a lens with grooves and with trace material deposited in the grooves.
Figure 5C:
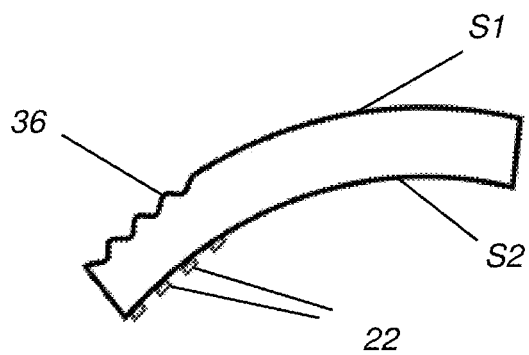
FIG. 5C shows a cross-sectional view of a lens with grooves and with trace material deposited on the opposite side of the lens.

The lens 10 can also be featured to improve sensitivity by increasing the amount of curvature change that is possible for corresponding IOP changes. As shown in the cross-sectional partial side view of FIG. 5A, embodiments of the present invention provide a contact lens 10 having one or more grooves 36 formed along the outer surface S1 and inner surface S2 of the lens 10 substrate. Grooves 36 enhance the flexure of lens 10 in response to changes in the shape of the eye. FIG. 5B shows grooves 36 that also have resistive traces 22 formed therein. This enables taking advantage not only of the additional flexibility of the lens afforded by the grooves, but also of the stress concentration at concave surfaces of the grooves. FIG. 5C shows a cross sectional side view of an embodiment of lens 10 in which grooves 36 are formed on one surface, shown here as outer surface S1, and traces 22 are formed on the opposite inner surface S2.

Figure 6A:
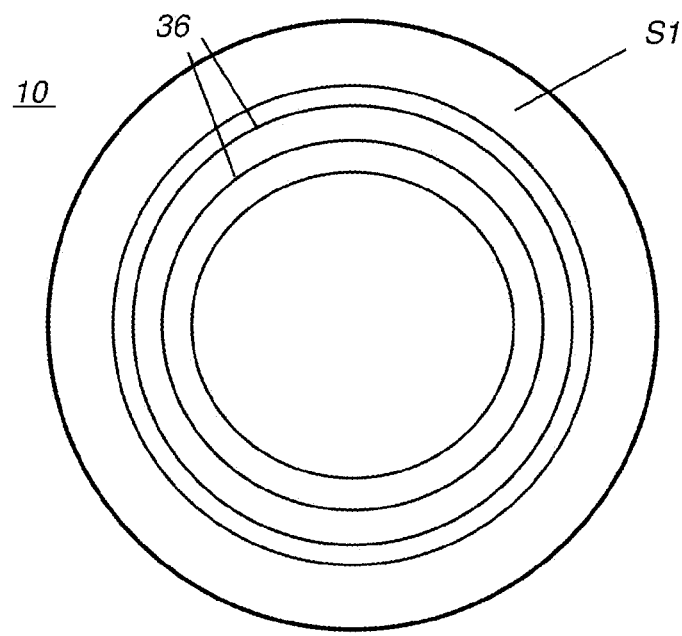
FIG. 6A shows a top view of a contact lens having grooves along its outer periphery.
Figure 6B:
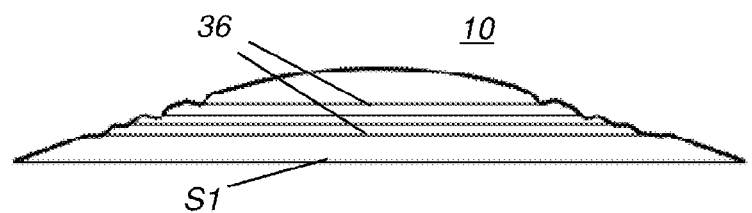
FIG. 6B is a side view of a contact lens having the arrangement of FIG. 6A.

Grooves 36 can be formed on either or both inner and outer surfaces S1 or S2. FIG. 6A shows a top view of a contact lens 10 having grooves 36 along outer surface S1. FIG. 6B is a side view of contact lens 10 having this arrangement.

Where grooves 36 are provided on one surface of the lens 10 substrate, two of the strain gauge 20 portions are located inside the limbus of the eye. The other two portions of strain gauge 20 are outside the limbus. When grooves 36 are provided on both surfaces S1 and S2, both paired strain gauge 20 portions are either inside the limbus or outside the limbus, or using any arrangement with two resistive traces inside the limbus and two resistive traces outside the limbus.

Obtaining Measurement Data

Strain gauge 20 measurements can be obtained in a number of ways. According to an embodiment of a measurement system 100 of the present invention shown in FIG. 7A, lens 10, worn by a patient 12 is connected to a signal monitor 40 that is in signal communication with the traces of gauge 20. Signal monitor 40 reads and stores measurement data from gauge 20 that is formed on lens 10. Signal monitor 40 is carried or worn by the patient. Signal monitor 40 may be battery powered or may be powered by any other means such as by wireless coupling with an external energy source or by an energy harvester, and has some amount of on-board logic circuitry and memory circuitry for obtaining and storing the measurement data. At a later time, signal monitor 40 then transfers its stored values to a computer or other type of host processor 42 that interprets and reports on the stored data. Data results may be displayed on a display 46 or printed, for example, and may be analyzed by software that tracks IOP for the patient.

Figure 7A:
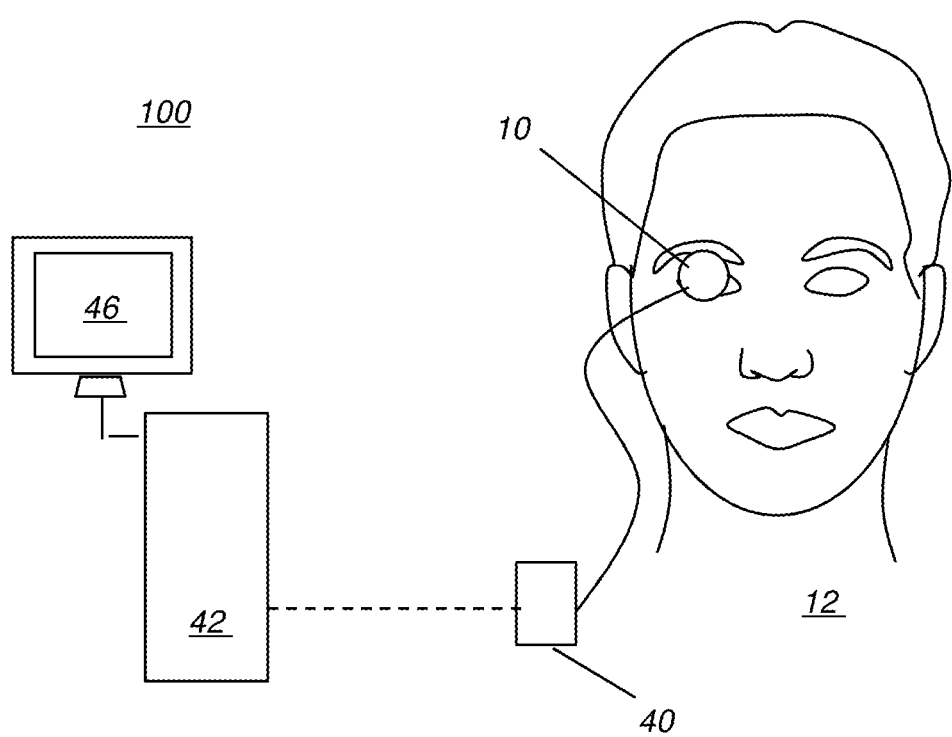
FIG. 7A is a schematic view that shows a measurement system with a contact lens connected to a monitor that is carried or worn by the patient and that temporarily stores results for that patient.
Figure 7B:
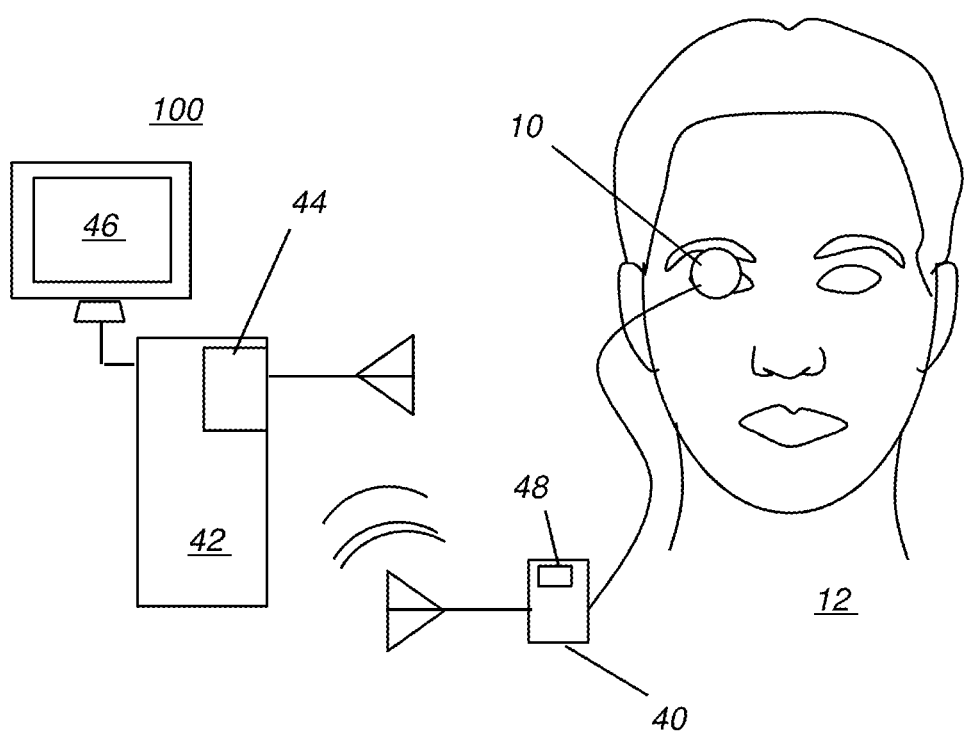
FIG. 7B is a schematic view that shows a measurement system with a contact lens connected to a monitor that communicates in wired or wireless fashion.

The schematic diagram of FIG. 7B shows an alternate embodiment of the present invention in which signal monitor 40 connects continuously with external host processor 42 for providing ongoing IOP monitoring. The connection between signal monitor 40 and host processor 42 can be wired or wireless. Wireless signal communication between signal monitor 40 and host processor 42 is shown in the diagram of FIG. 7B. A transceiver 44 is in signal communication with host processor 42 and in wireless signal communication with a signal conditioning and processing circuit 48 that is part of signal monitor 40.

Figure 7C:
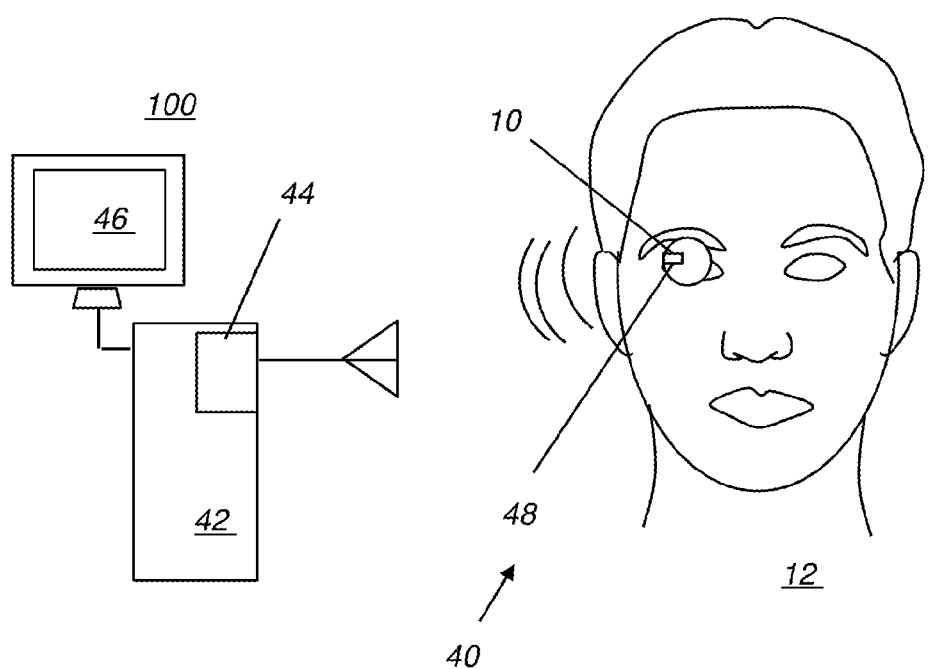
FIG. 7C is a schematic view that shows a measurement system with a contact lens that is worn by the patient and that communicates wirelessly to a monitoring apparatus.

The schematic diagram of FIG. 7C shows another alternate embodiment of the present invention in which host processor 42 uses a transceiver 44 for wireless communication with signal monitor 40. Here, monitor 40 includes signal conditioning and processing circuit 48 that incorporates a wireless transponder and is responsive to wireless transmission. According to an embodiment of the present invention, signal monitor 40 and its signal conditioning and processing circuit 48 are formed and mounted on inner surface S2 or, alternately, on outer surface S1. Upon receipt of an encoded radio frequency (RF) signal from transceiver 44, the transponder circuitry in signal conditioning and processing circuit 48 obtains the measurement of the value obtained from the gauge by signal monitor 40 on contact lens 10, then encodes and transmits measurement data to transceiver 44. Signal conditioning and processing circuit 48 is energizable to provide an input voltage and current to the Wheatstone bridge, and an output signal that is indicative of a measurement obtained by a voltage sensor that is incorporated into signal conditioning and processing circuit 48. According to an embodiment of the present invention, a radio frequency (RF) signal received by signal conditioning and processing circuit 48 is converted to an electrical current that is provided to gauge 20 for IOP sensing. Power received from the RF signal also provides sufficient energy for signal measurement, conversion to a data value, and transmission back to the originating transceiver. Obtaining the needed power for communication and for some measure of signal processing from transceiver transmission to a transponder is known to those skilled in the wireless communication arts.

For the embodiments of the present invention that are shown in FIGS. 7A, 7B, and 7C, the voltage source for gauge measurement and signal encoding may alternately be provided by any suitable power source, which may be a battery.

Figure 8A:
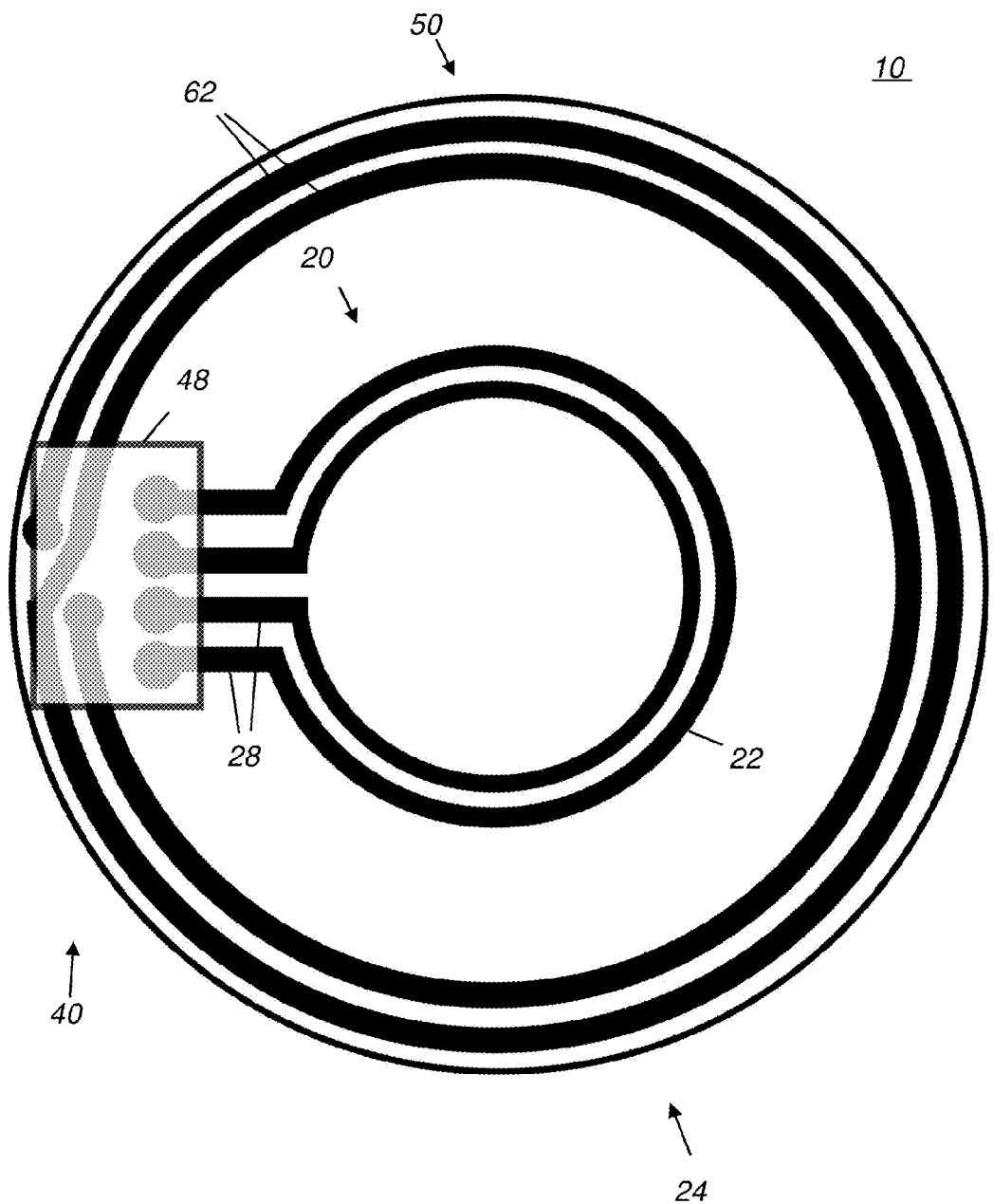
FIG. 8A is a top view that shows a contact lens having signal conditioning and processing circuit suitable for the embodiment of the present invention that is shown in FIG. 7C.

The top view of FIG. 8A shows contact lens 10 having monitor 40 with signal conditioning and processing circuit 48, suitable for the embodiment of the present invention that is shown in FIG. 7C. Gauge 20 uses resistive traces 22. Coil traces 62 form a coil 50 that serves as the antenna for signal conditioning and processing circuit 48 communication at radio frequencies (RF) or other suitable frequencies. Two traces 62 are shown in FIG. 8A and in subsequent figures of this disclosure; a single trace 62 or more than two traces 62 can alternately be provided, formed on one or both surfaces of contact lens 10. Signal conditioning and processing circuit 48 of monitor 40 includes signal sensing and conditioning circuitry such as an analog to digital (A/D) converter that is in signal communication with the first and second arcuate patterns of resistive traces of gauge 20 and that provides a signal indicative of the lens shape according to electrical current through the first and second arcuate patterns of resistive traces.

Figure 8B:
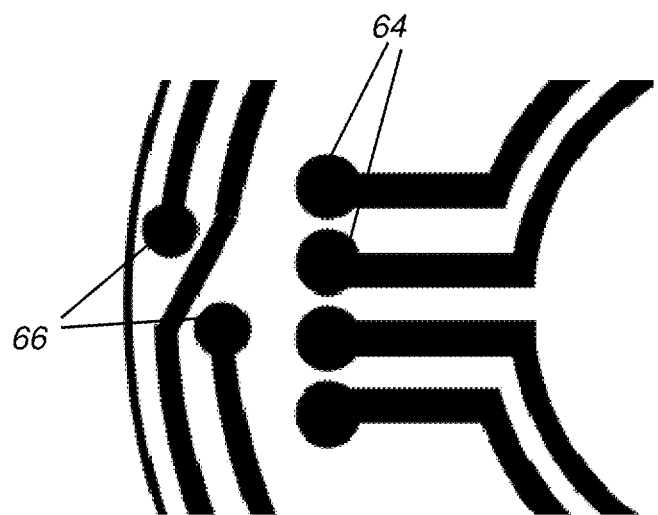
FIG. 8B is an enlarged view that shows the contact pattern of connection pads for the signal conditioning and processing circuit site in FIG. 8A.

The enlarged view of FIG. 8B shows the contact pattern of connection pads 64 and 66 for the signal conditioning and processing circuit 48 site in FIG. 8A. Pads 64 are for strain gauge 20 connections. Pads 66 are for RF antenna coil 50. This arrangement of pads 66 can be used for flip-chip bonding or wire bonding, for example.

Figure 9A:
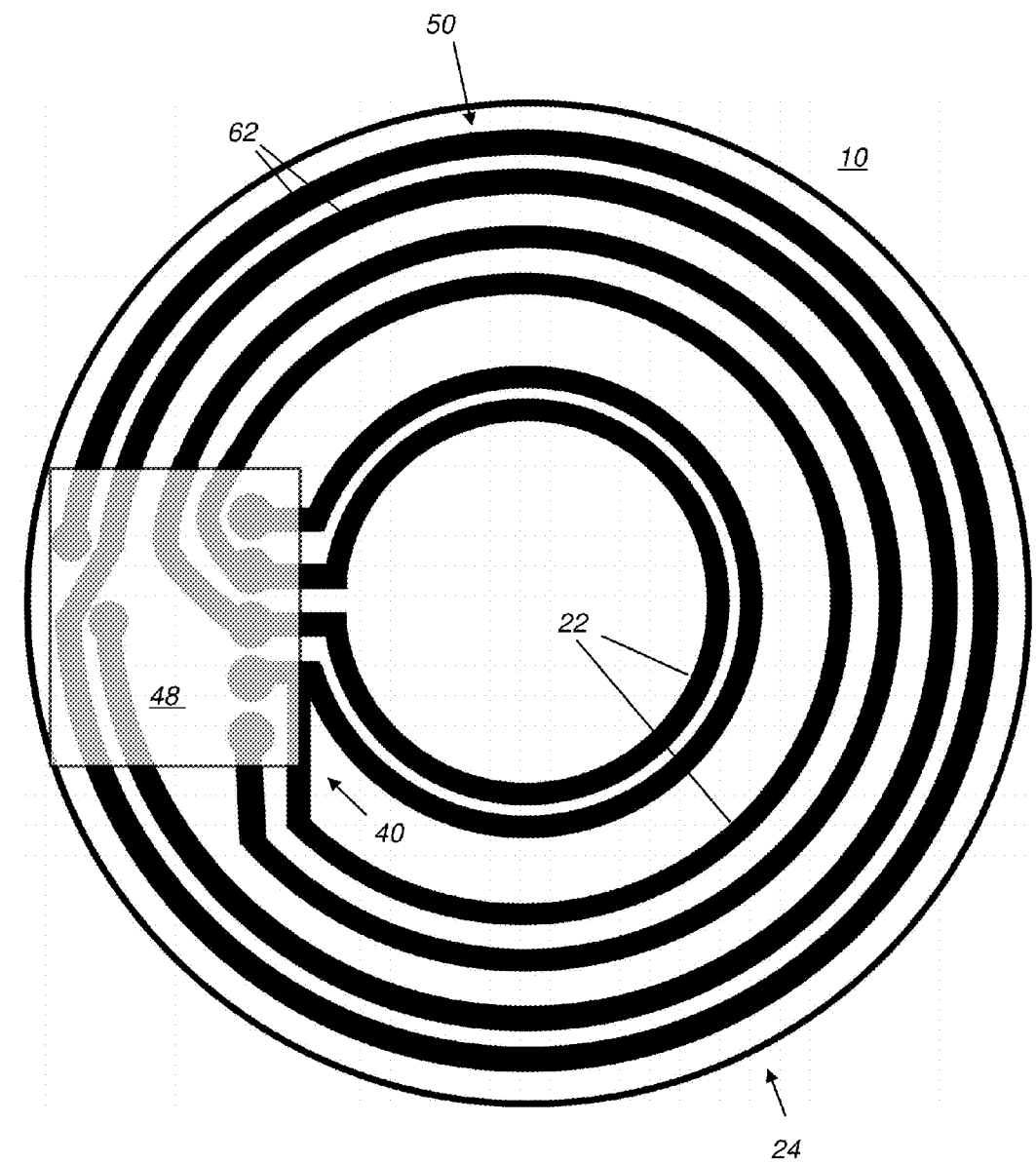
FIG. 9A is a schematic view that shows the arrangement of components and circuit traces along a single surface according to an embodiment of the present invention.

The applied traces can be from opaque or transparent materials. The narrow dimensions and/or the location of the traces make it possible to apply opaque materials without adverse effects to the patient's vision. Multiple layers can be applied. FIG. 9A is a schematic view that shows the arrangement and connections between gauge 20 portions with other elements of contact lens 10, including signal conditioning and processing circuit 48 and coil 50 for RF communication on outer surface S1.

Figure 9B:
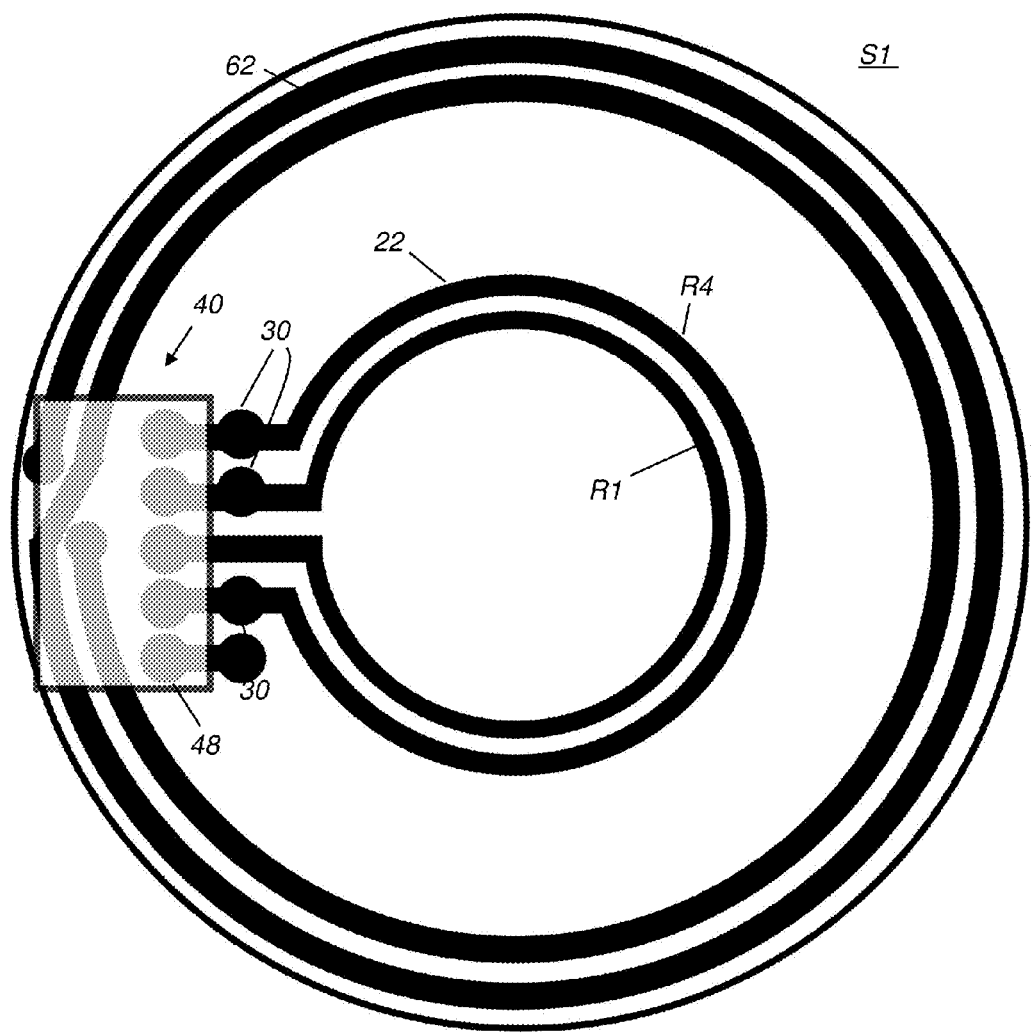
FIG. 9B is a schematic view that shows components and traces formed on one surface according to an alternate embodiment of the present invention.
Figure 9C:
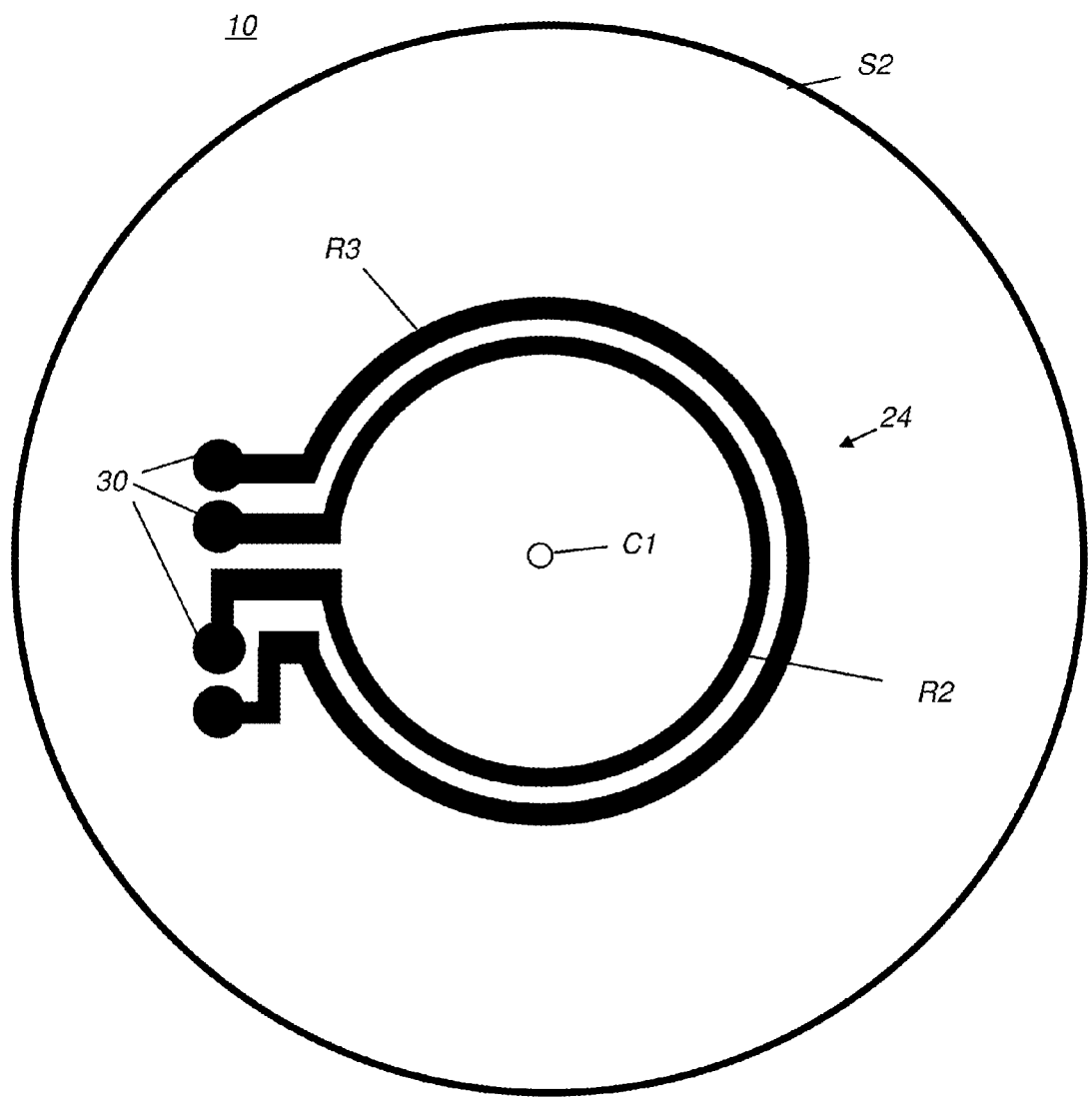
FIG. 9C is a schematic view that shows components and traces formed on the opposite surface for the alternate embodiment of the present invention shown in FIG. 9B, using through-hole vias.
Figure 9D:
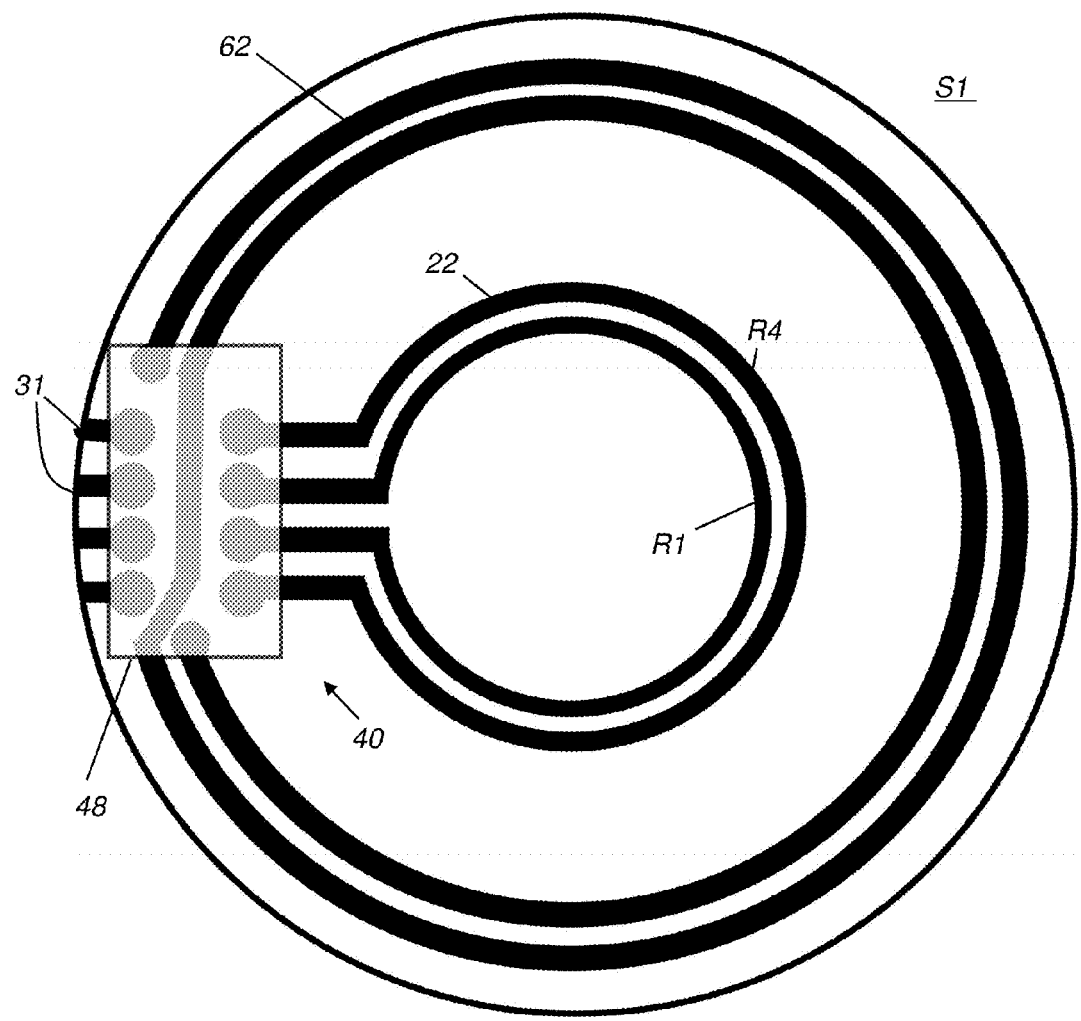
FIG. 9D is a schematic view that shows components and traces formed on one surface according to an alternate embodiment of the present invention using wrap-around vias.
Figure 9E:
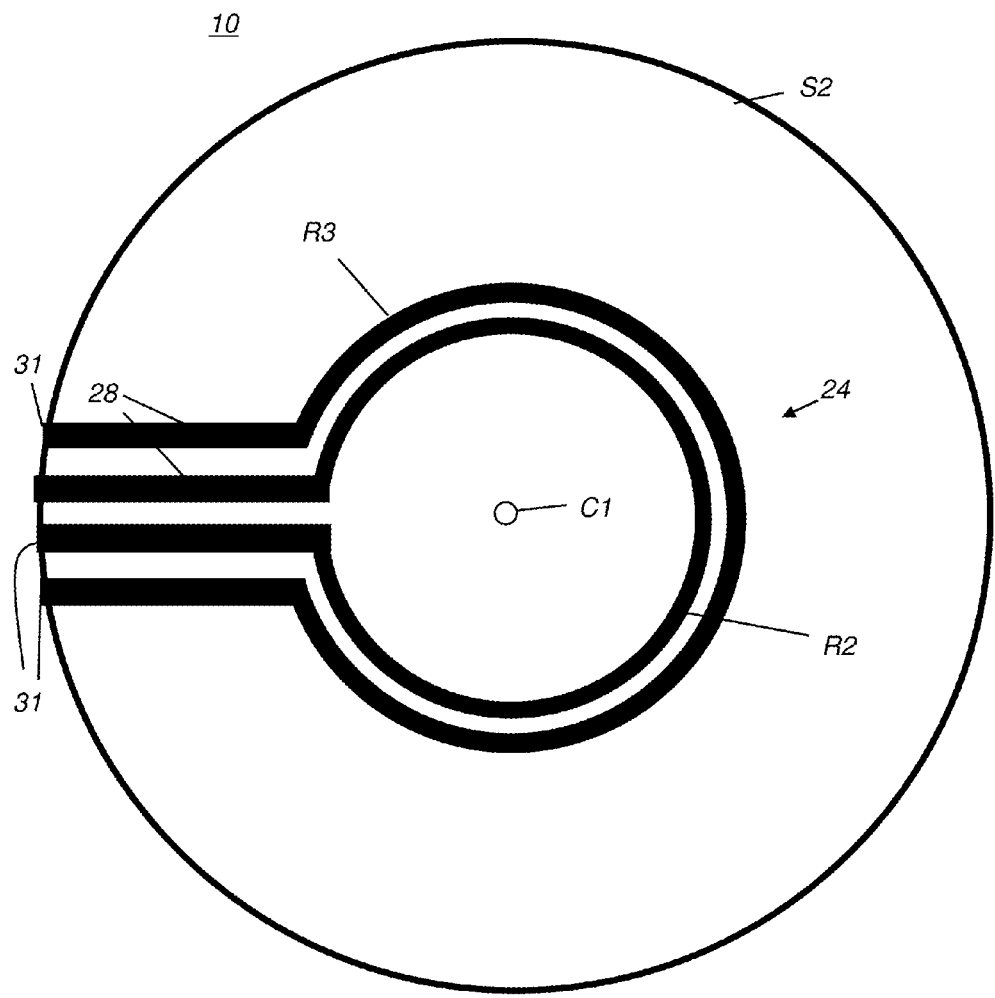
FIG. 9E is a schematic view that shows components and traces formed on the opposite surface for the alternate embodiment of the present invention shown in FIG. 9D, using wrap-around vias.

As described previously, the indicated traces and other features for the complete contact lens 10 shown in FIG. 9A can be provided on the same surface S1 or S2 of lens 10 or can be distributed between surfaces S1 and S2 with the necessary interconnects between surfaces. FIGS. 9B and 9C show an alternate embodiment of the present invention, wherein there are portions of strain gauge 20 formed on each of the surfaces S1 and S2. FIGS. 9D and 9E show an alternate embodiment of the present invention using wrap-around vias 31 for making connections between surfaces S1 and S2.

According to yet another alternate embodiment of the present invention, one or more coil traces 62 of coil 50 are on opposite surfaces. For example, half of the coil traces 62 are formed on surface S1, the other half of the coil traces 62 are formed on the opposite surface S2. As noted previously with respect to resistive traces 22, coil traces 62 on opposite surfaces can be visually superimposed or overlapping with respect to the optical path for the patient.

According to an embodiment of the present invention, signal conditioning and processing circuit 48 of signal monitor 40 is a micro-controller that is in signal communication with resistive traces 22 of the strain gauge 20. Signal conditioning and processing circuit 48 can have a number of functional components, including analog-to-digital converter, RF signal transponder, control logic circuitry, stored program, and memory circuitry for data value storage, for example.

Fabrication

Grooves 36 (FIGS. 5A-6B) can be molded or formed into an existing lens 10 substrate using a lathe or similar machining apparatus. Nominal depth of groove 36 ranges from 50-100 microns. Radius and sidewall inclination values are maintained to minimize problems with stress and handling.

Figure 10A:
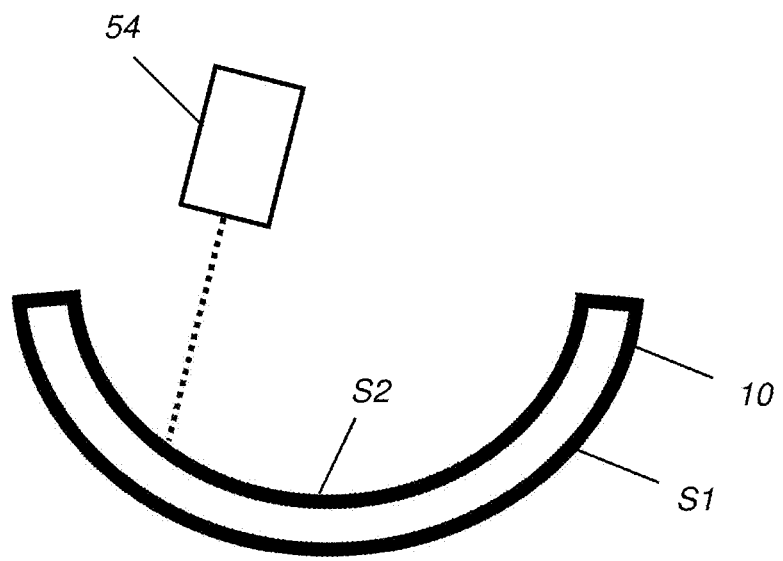
FIG. 10A shows materials application on the inner surface of the lens using an inkjet printhead.
Figure 10B:
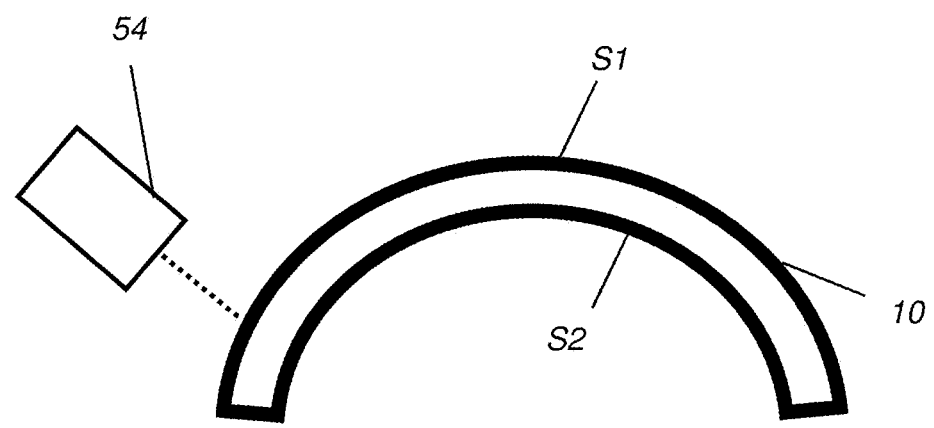
FIG. 10B shows materials application on the outer surface using an inkjet printhead.
Figure 10C:
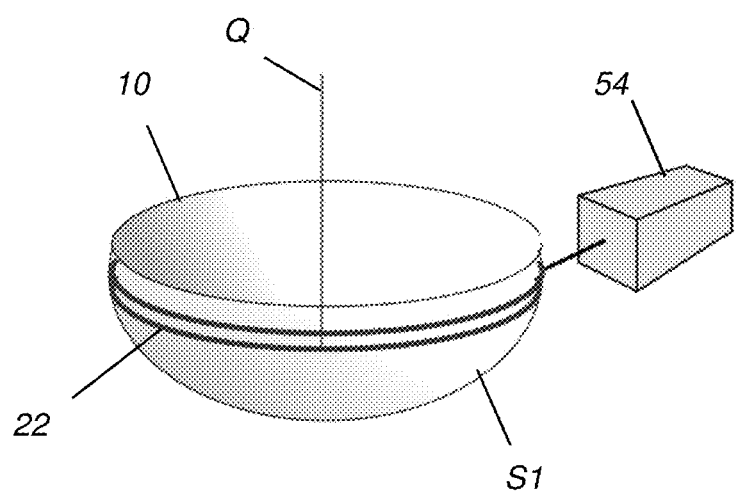
FIG. 10C shows inkjet application of traces by rotating the lens about its axis.

Consistent with an embodiment of the present invention, inkjet printing is used for forming the resistive and conductive traces on one or both surfaces of contact lens 10. By way of example, FIG. 10A shows materials application on inner surface S2 using an inkjet printhead 54. FIG. 10B shows materials application on outer surface S1 using inkjet printhead 54. FIG. 10C shows inkjet application of traces 22 by orbiting printhead 54 about contact lens 10 or, alternately, by rotating the lens 10 about its axis Q, with printhead 54 held stationary. According to an alternate embodiment, traces 22 can be formed by printing into a mold prior to forming the lens from its substrate material.

Forming a pattern of conductive and resistive traces by inkjet printing is known to those skilled in the printed-circuit fabrication arts. The process of forming traces involves printing the material onto a substrate, followed by a curing process, which may use heat, light, or chemical energy for forming the final trace pattern.

According to an embodiment of the present invention, the same ink formulation is used for forming both conductive traces 28 and resistive traces 22, as well as for forming coil traces 62. Traces 22, 28, and 62 can be formed from conductive inks formed from copper, silver, platinum, and other conductive metals. When the same material is used and different resistive properties are needed, the thickness (height above the surface from build-up of deposited material) and width (along the curved surface) of the traces can be varied accordingly. Exemplary values using a silver-based ink are as follows:

Resistive trace 22: 0.1-0.2 μm height; 10-20 μm width.
Conductive trace 28 (interconnects): 1-2 μm height; 20-40 μm width.
Coil trace 62: 10-20 μm height; 40-80 μm width.
Through-hole vias 30: 10-20 μm thickness of printed material, hole filled; nominal via diameter 20-40 μm.

As can be seen from this listing, resistive and conductive traces can differ in thickness by an order of magnitude or more.

Resistive traces 22 for gauge 20 can alternately be formed from materials that exhibit higher resistivity and/or exhibit a higher gauge factor (that is, a higher sensitivity of resistor value on strain). According to an alternate embodiment of the present invention, different materials are used for conductive vs. resistive traces. For example, a combination of platinum for the resistor elements and silver for all other elements is feasible and would make use of the slightly higher resistivity and gauge factor, and slightly lower temperature coefficient, of platinum compared with silver. This combination would also make use of the higher conductivity of silver, at the expense of additional manufacturing cost compared with using the same material for all elements.

Nominal through-hole via 30 dimensions are 20 microns in diameter. Vias 30 could be smaller or larger; the nominal value given herein can be modified depending on the methods used for forming the through-hole. The via should be sufficiently narrow so that depositing conductive trace material closes the via. This allows maintaining a tear film beneath the lens 10. Vias 30 can be formed using laser drilling or by some other method.

It should also be noted that inkjet printing can also be used to form one or more intermediary non-conducting layers between traces 22, 28, and 62, thereby isolating the different types of signals used and expanding the range of possible circuit pattern arrangements on one or both surfaces. With a layer or pattern of insulating material deposited appropriately, for example, traces 62 used for RF coil 50 can pass above or below conductive traces 28 at one or more locations. This would form a multilayer structure of conductive and resistive traces 22, 28, and 62 on one or both surfaces S1 and S2 of contact lens 10. Such an arrangement can help to adapt to connection requirements of signal conditioning and processing circuit 48, for example.

The lens 10 substrate is a moldable plastic material such as silicone, or TPX (Polymethylpentene (PMP)).

According to an alternate embodiment of the present invention, lens 10 is itself formed using a 3-dimensional printing process. This builds up the lens 10 substrate material in successive layers and allows the thickness of lens 10 to be varied at different points. In addition, forming the lens using additive printing processes also allows grooves 36 to be generated as the lens is formed, rather than requiring a separate operation for removal of lens material.

A gel is typically applied to one or more surfaces of lens 10 for wearing by the patient.

The invention has been described in detail with particular reference to certain preferred embodiments thereof, but it will be understood that variations and modifications can be effected within the scope of the invention as described above, and as noted in the appended claims, by a person of ordinary skill in the art without departing from the scope of the invention. For example, any of a number of types of layers could alternately be added, including materials for tinting the lens color, for example.

Using an embodiment of the present invention, a measurement apparatus for IOP measurement can be custom designed and fabricated for each patient. Various types of materials can be used for forming traces onto curved optical surfaces. Thus, what is provided is an apparatus and method for non-invasive monitoring of intraocular pressure.

The invention claimed is:

1. A monitoring apparatus for an eye of a patient, comprising:
   a) a soft contact lens formed of a transparent substrate and having a center;
   b) a first arcuate pattern of resistive traces printed onto an outer surface of the lens substrate and concentric about the center of the lens;
   c) a second arcuate pattern of resistive traces printed onto an inner surface of the lens substrate and concentric about the center of the lens and wherein, with respect to the eye of the patient, traces of the first and second arcuate patterns are visually aligned;
   d) one or more conductive traces printed on the lens, wherein the one or more conductive traces connect the first pattern to the second pattern, and
   e) a signal monitor that is in signal communication with the first and second arcuate patterns of resistive traces and that is energizable to provide a signal indicative of the lens shape according to electrical current through the first and second arcuate patterns of resistive traces.

2. The monitoring apparatus of claim 1 further having a plurality of concentric circular grooves formed in the substrate.

3. The monitoring apparatus of claim 2 wherein at least a portion of the first or second arcuate pattern of resistive traces lie within the concentric circular grooves.

4. The monitoring apparatus of claim 1 wherein the signal monitor comprises a transponder that is coupled to the inner or outer surface of the lens.

5. The monitoring apparatus of claim 1 further comprising at least one antenna coil formed on the outer surface of the lens and in signal communication with the signal monitor.

6. The monitoring apparatus of claim 1 further comprising at least one antenna coil formed on the inner surface of the lens and in signal communication with the signal monitor.

7. The monitoring apparatus of claim 1 wherein at least one or more of the one or more conductive traces connects through a via between the inner and outer surfaces.

8. The monitoring apparatus of claim 1 wherein at least one or more of the one or more conductive traces extends around an edge between the inner and outer surfaces.

9. The monitoring apparatus of claim 1 wherein the signal monitor further comprises a memory.

10. The monitoring apparatus of claim 2 wherein at least a portion of the first or second arcuate patterns of resistive traces are in alignment with some of the plurality of concentric circular grooves.

11. The monitoring apparatus of claim 1 wherein the resistive and conductive traces are formed from the same material and wherein the conductive traces differ in thickness from the resistive traces by more than a factor of two.

12. The monitoring apparatus of claim 1 wherein the resistive traces are formed from a first material and the conductive traces are formed from a second material that is different from the first material.

13. The apparatus of claim 1 wherein the signal monitor is connected to the contact lens by a wire.

14. A method for forming a monitoring apparatus for the eye, the method comprising:

a) forming a soft contact lens of a transparent substrate and having a center and having a plurality of concentric circular grooves in the substrate that encircle the center of the lens;
b) depositing and curing a first arcuate pattern of resistive traces onto an outer surface of the lens substrate and wherein the first arcuate pattern is concentric about the center of the lens;
c) depositing and curing a second arcuate pattern of resistive traces onto an inner surface of the lens substrate and wherein the second arcuate pattern is concentric about the center of the lens and is visually aligned with the first arcuate pattern;
d) depositing and curing one or more conductive traces on the lens that connect the first pattern to the second pattern, and
e) coupling a signal monitor to the lens, wherein the signal monitor is in signal communication with the first and second arcuate patterns of resistive traces;
and
f) energizing the signal monitor to obtain a signal indicative of the lens shape according to electrical current through the first and second arcuate patterns of resistive traces.

15. The method of claim 14 wherein depositing traces is performed using an inkjet printing process.

16. The method of claim 15 wherein curing the deposited ink traces uses light energy or thermal energy or a combination of both light and thermal energy.

17. The method of claim 14 wherein depositing and curing either or both first and second arcuate patterns comprises depositing a material within at least a portion of the concentric circular grooves.

* * * * *